United States Patent
Ivany

(10) Patent No.: US 7,458,950 B1
(45) Date of Patent: Dec. 2, 2008

(54) ANKLE FOOT ORTHOSIS

(76) Inventor: Michael Ivany, 279 N. Broadway, Yonkers, NY (US) 10701

( * ) Notice: Subject to any disclaimer, the term of this patent is extended or adjusted under 35 U.S.C. 154(b) by 233 days.

(21) Appl. No.: 11/174,064

(22) Filed: Jul. 1, 2005

Related U.S. Application Data

(60) Provisional application No. 60/584,576, filed on Jul. 2, 2004.

(51) Int. Cl.
A61F 5/00 (2006.01)
A43C 11/00 (2006.01)
A43B 23/00 (2006.01)

(52) U.S. Cl. .................. 602/28; 602/23; 602/27; 602/29; 602/30; 602/5; 36/50.1; 36/136

(58) Field of Classification Search ............... 602/27, 602/28, 24, 26, 23.5, 30; 36/50.1, 136
See application file for complete search history.

(56) References Cited

U.S. PATENT DOCUMENTS

| | | | |
|---|---|---|---|
| 246,984 A | 9/1881 | Stillman | |
| 839,223 A | 12/1906 | Stevens | |
| 1,402,282 A | 1/1922 | Chevrier | |
| 2,439,100 A | 4/1948 | Richards | |
| 2,477,591 A | 8/1949 | Follis | |
| 2,557,603 A | 6/1951 | Invidiato | |
| 2,584,010 A | 1/1952 | Goffredo | |
| 2,663,294 A | 12/1953 | Harison | |
| 2,712,310 A | 7/1955 | Giambra | |
| 2,973,757 A | 3/1961 | Katthoefer | |
| 3,086,521 A | 4/1963 | Desai | |
| 3,504,668 A | 4/1970 | Boudon | |
| 3,527,209 A | 9/1970 | Baker | |
| 3,589,359 A | 6/1971 | Hill | |
| 3,827,430 A | 8/1974 | Fadden | |
| 3,859,991 A | 1/1975 | Theodores | |
| 4,329,982 A | 5/1982 | Heaney | |
| 4,459,980 A | 7/1984 | Perser | |
| 4,550,721 A | 11/1985 | Michel | |
| 4,566,447 A * | 1/1986 | Deis | 602/28 |
| 4,651,723 A | 3/1987 | Satoh | |
| 4,817,589 A | 4/1989 | Wertz | |
| 5,092,319 A | 3/1992 | Grim | |
| 5,219,324 A | 6/1993 | Hall | |
| 5,277,699 A | 1/1994 | Williamson | |
| 5,291,904 A * | 3/1994 | Walker | 128/882 |
| 5,445,603 A | 8/1995 | Wilkerson | |
| 5,472,414 A | 12/1995 | Detty | |
| 5,860,423 A | 1/1999 | Thompson | |
| 6,059,744 A * | 5/2000 | Hardt | 602/62 |
| 6,102,881 A | 8/2000 | Quackenbush | |
| 6,126,625 A * | 10/2000 | Lundberg | 602/27 |

(Continued)

*Primary Examiner*—Patricia Bianco
*Assistant Examiner*—Tarla Patel
(74) *Attorney, Agent, or Firm*—Seth Natter; Natter & Natter

(57) ABSTRACT

An ankle foot orthosis for remediation of foot drop symptoms includes a flexible cuff formed of a panel having an inner foam substrate to which is bonded an outer layer of stretchable fabric having looped fibers. A pair of dorsiflexor support straps include lace segments which are threaded through lower shoelace eyelets. The lace segments are tied together at the shoe. A hook element fastener strip is attached to the opposite end of each lace segment. The support straps cross one another over the shoe vamp and the fastener strips are secured to the sides and wrapped about the rear of the cuff.

16 Claims, 4 Drawing Sheets

U.S. PATENT DOCUMENTS 6,299,587 B1    10/2001  Birmingham
6,467,193 B1 *  10/2002  Okajima ........................ 36/10
6,908,445 B2     6/2005  Watts
2005/0070833 A1 *  3/2005  Shields ......................... 602/27
2005/0177083 A1 *  8/2005  Heil ............................. 602/27

* cited by examiner

ANKLE FOOT ORTHOSIS

RELATED APPLICATIONS

This application claims the benefit of U.S. Provisional Application No. 60/584,576, filed Jul. 2, 2004.

BACKGROUND OF THE INVENTION

1. Field of the Invention

This invention relates generally to orthotics and more particularly to an ankle foot orthosis for remediation of foot drop symptoms.

2. Antecedents of the Invention

Foot drop, drop foot and foot dangle are terms which have been employed to describe ankle and toe dorsiflexor paresis resulting in the inability to raise the foot at the ankle, such that the foot inclines toward and scrapes the ground when walking.

The etiology of foot drop may be traced to a plurality of factors including neurological, e.g. peroneal nerve damage, muscular, e.g. dorsiflexor injury and anatomic dysfunction, as well as combinations thereof.

A common remediation technique for foot drop involved the employment of an ankle foot orthosis. These devices were costly and often required professional fitting and customized shoes. Professional fitting procedures of some devices required the taking of impressions of the affected foot. There were significant delays between the fitting and receipt of the customized orthosis.

Some devices were configured to completely lock the ankle joint and constrained normal ankle joint motion in ranges other than dorsiflexion, resulting in discomfort and restricted gait. Discomfort was also associated with those ankle foot orthoses which included components inserted into the shoe itself.

Prior ankle foot orthoses also included components which surrounded the calf or ankle to support the affected foot and often caused irritation of the ankle or calf and muscle strain.

Generally, prior ankle foot orthoses were unsightly, which detracted from the beneficial results which might have been achieved in alleviating steppage gait.

SUMMARY OF THE INVENTION

An ankle foot orthosis for the treatment of ankle dorsiflexor paresis commonly referred to as foot drop, drop foot or foot dangle comprises a flexible laminated cuff formed of a panel having a compressible and stretchable inner foam substrate to which is bonded an outer layer of stretchable fabric. The cuff is wrapped about the ankle, directly over skin, over a sock, or over the ankle portion of a high topped shoe or boot and secured to looped fibers of the fabric layer by a hook element fastener strip.

A pair of dorsiflexion support straps include lace segments which are threaded through registered lower shoelace eyelets of a conventional shoe. The lace segments are tied together at the shoe. Fixed to the opposite ends of each lace segment is a hook element fastener strip.

The support straps cross one another over the shoe vamp and the fastener strips are secured to the sides and wrapped about rear of the cuff, after the foot has been positioned at an appropriate angle to adequately tension the straps for dorsiflexor support. The cuff and support straps may be selected from a variety of colors to inconspicuously match or coordinate with one's shoe color or the cuff color is selected to match one's socks.

From the foregoing compendium, it will be appreciated that it is an aspect of the present invention to provide an ankle foot orthosis of the general character described which is not subject to the disadvantages of the antecedents of the invention aforementioned.

A feature of the present invention is to provide an ankle foot orthosis of the general character described which inconspicuously alleviates foot drop symptoms.

A consideration of the present invention is to provide an ankle foot orthosis of the general character described which is comfortable to wear.

An additional aspect of the present invention is to provide an ankle foot orthosis of the general character described which is relatively low in cost.

Another feature of the present invention is to provide an ankle foot orthosis of the general character described which does not require professional fitting.

A further consideration of the present invention is to provide an ankle foot orthosis of the general character described which is free of shoe inserts.

To provide an ankle foot orthosis of the general character described which functions with conventional shoes is yet a further feature of the present invention.

Another aspect of the present invention is to provide an ankle foot orthosis of the general character described which can be easily filled with all of the shoes in one's wardrobe.

To provide an ankle foot orthosis of the general character described which is available in various colors to match or coordinate with a wearer's shoes and/or socks is yet a further feature of the present invention.

Another consideration of the present invention is to provide an ankle foot orthosis of the general character described which is ready to use.

A still further feature of the present invention is to provide an ankle foot orthosis of the general character described which is light in weight.

A still further aspect of the present invention is to provide an ankle foot orthosis of the general character described which is well suited for an independent lifestyle.

To provide an ankle foot orthosis of the general character described which permits ankle joint mobility in unsupported directions is a further consideration of the present invention.

Another feature of the present invention is to provide an ankle foot orthosis of the general character described which is washable.

To provide an ankle foot orthosis of the general character described which is readily adapted for mass production fabrication is another aspect of the present invention.

A consideration of the present invention is to provide an ankle foot orthosis of the general character described which may be used over extended periods without fatigue or strain.

An additional feature of the present invention is to provide an ankle foot orthosis of the general character described which is adjustable to accommodate various ankle/foot dimensions.

To provide an ankle foot orthosis of the general character described which can be employed in conjunction with shoes having lace eyelets is a still further feature of the present invention.

An additional aspect of the present invention is to provide an ankle foot orthosis of the general character described having a generally low profile and inconspicuous appearance.

BRIEF DESCRIPTION OF THE DRAWINGS

In the accompanying drawings in which is shown some of the various possible exemplary embodiments of the invention.

DESCRIPTION OF THE PREFERRED EMBODIMENT

Figure 1:
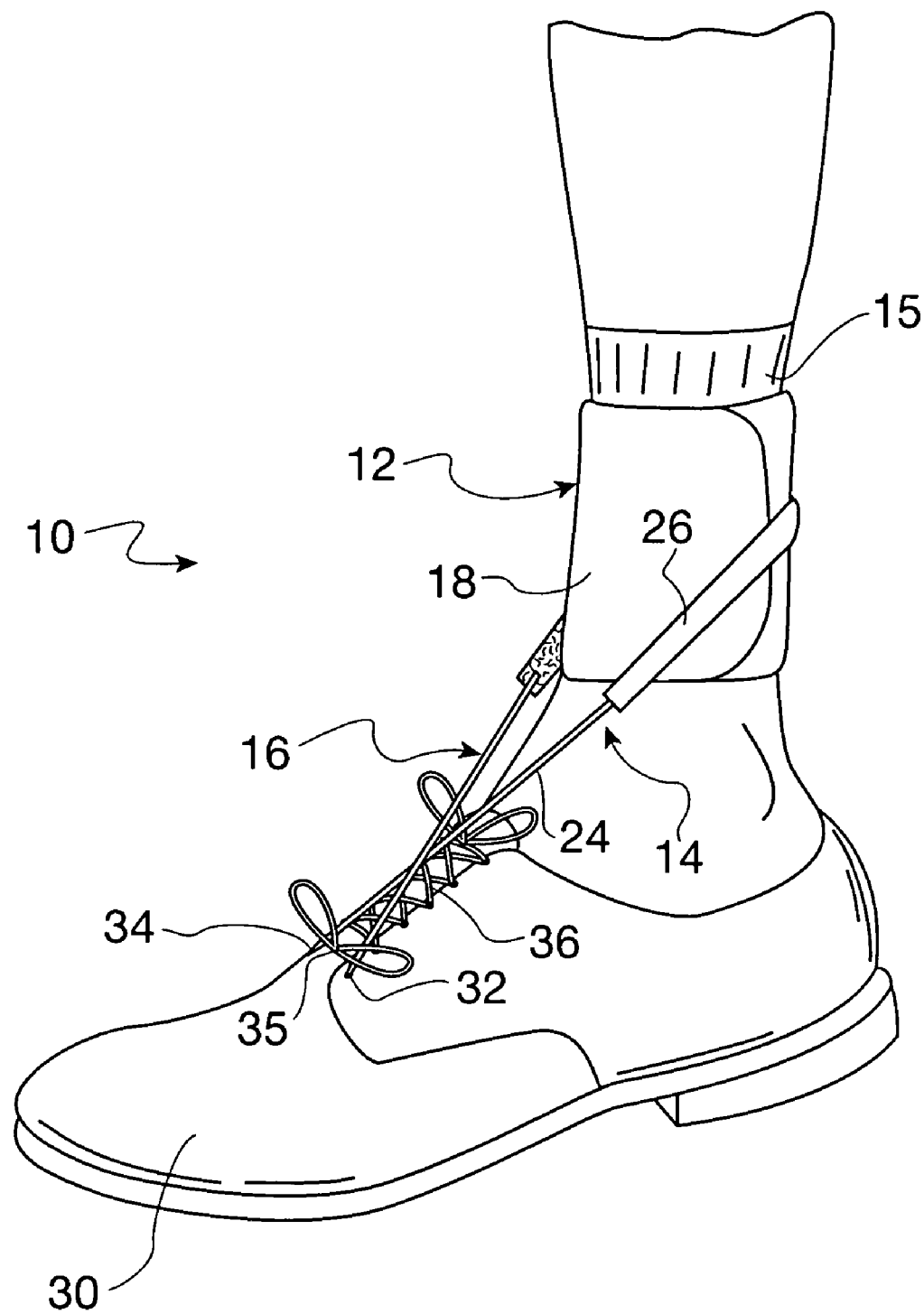
FIG. 1 is a perspective illustration of a fitted ankle foot orthosis constructed in accordance with and embodying the invention and showing a stretchable cuff wrapped about an ankle and a pair of support straps extending from eyelets of a shoe, with each strap having a hook type fastener strip anchored to the cuff.

Referring now in detail to the drawings, the reference numeral 10 denotes generally an ankle foot orthosis constructed in accordance with and embodying the invention. Pursuant to the invention, the ankle foot orthosis 10 includes a stretchable cuff 12 which is wrapped about the ankle and a pair of dorsiflexion support straps 14, 16 which are connected between the vamp of a shoe and the cuff 12.

The dorsiflexion support straps comprise a medial support strap 14, which is connected to the medial aspect of a shoe vamp and a lateral support strap 16, which is connected to the lateral aspect of a shoe vamp.

The cuff 12 comprises a stretchable, padded, generally rectangular panel formed of a stretchable fabric layer 18, having exposed looped fibers on its outer surface, bonded to a stretchable foam substrate 20. The fabric layer 18 may have a thickness in the order of 1½ mm, while the foam substrate 20 may have a thickness in the order of 4 mm.

The cuff panel may comprise a compressible closed cell foam neoprene substrate such as R-1400-N, available from Rubberlite, Inc. of Huntington, W. Va. or an open cell polyurethane foam substrate such as that sold under the mark HYPUR-CEL®, also available from Rubberlite, Inc., or BREATH-O-PRENE®, B-25-0102, available from Accumed Technologies Inc. of Buffalo, N.Y.

The fabric layer 18 and foam substrate 20 possess the requisite stretchability and resilience to enable the cuff 12 to be comfortably wrapped and secured about a user's ankle and conform to the shape thereof. Employment of a closed cell foam substrate 20 provides therapeutic warmth to the ankle joint. The cuff 12 may be wrapped over a sock 15, to permit evaporation and adequate airflow around the ankle joint and reduce irritation. The employment of open cell foam as a substrate 20 also facilitates evaporation and airflow around the ankle.

Figure 2:
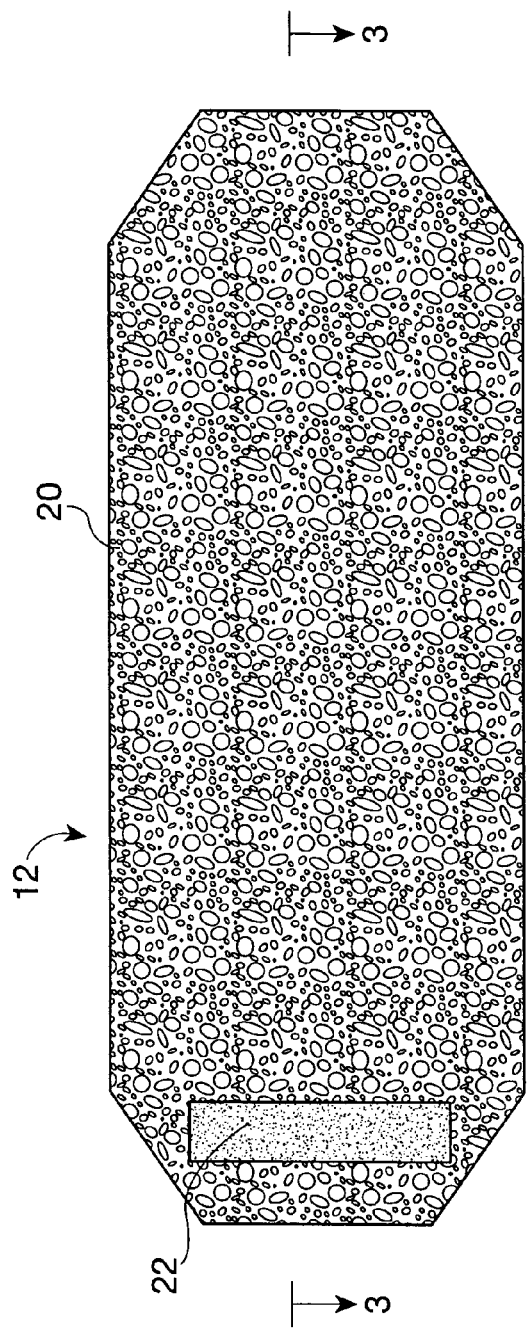
FIG. 2 is an enlarged scale interior plan view of the cuff and showing a foam substrate and a hook type fastener strip secured adjacent one end thereof.
Figure 3:
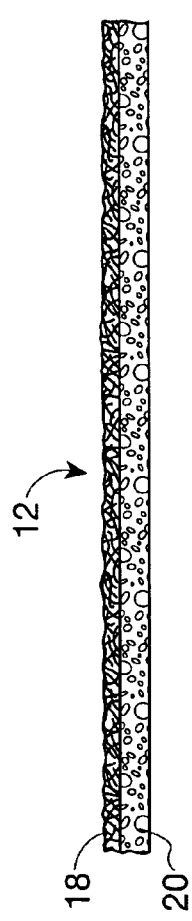
FIG. 3 is an enlarged scale fragmentary sectional view through the cuff, the same being taken substantially along the line 3-3 of FIG. 2 and illustrating a layer of stretchable fabric bonded to the foam substrate.

As will be noted from an examination of FIG. 2, the cuff panel is generally rectangular in shape. It has been found that a panel height of 12-15 cm and a panel length in the order of 40 cm provides sufficient coverage for wrapping about a variety of ankle sizes.

Secured over a portion of the foam substrate 20 adjacent one end of the cuff 12 is a hook fastener strip 22 which may be stitched to the cuff. In the event the cuff is to be worn by one with a relatively small ankle, the opposite end of the cuff may be trimmed with scissors so as to avoid excessive overlapping.

As previously mentioned, the cuff 12 is wrapped about the wearer's ankle and secured in position, as illustrated in FIG. 1 and FIGS. 7 through 9, with the hook fastening strip 22 having hook elements engaging the exposed loop fibers of the fabric layer 18. Hook and loop fastener systems of this type are commonly known and are available from, for example, Velcro Industries. It should be noted that for the purpose of simplification, the hook fastener strip 22 has not been illustrated in FIG. 8.

The stretchable cuff 12 instantly assumes a snug fit, conforming to the anatomical shape of the ankle joint, with the resilient, compressible foam substrate providing cushioning. The face of the foam substrate 20 preferably has a tack quality to facilitate adherence over the sock 15 or the user's skin and augmented resistance against sliding down the ankle.

Figure 4:
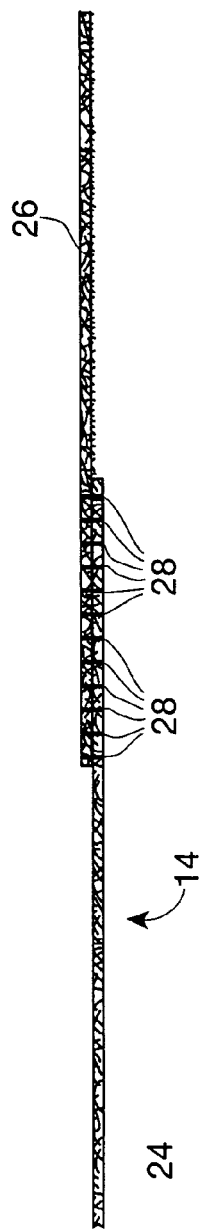
FIG. 4 is a fragmentary longitudinal sectional view through a support strap and illustrating the hook type fastener strip overlapping an end of a lace segment and secured thereto by stitching.

With reference now to FIG. 4, wherein a fragment of the medial support strap 14 is illustrated in enlarged scale cross section, it should be noted that the support strip 14 includes a lace segment 24 and a hook fastener strip 26, which overlaps an end area of the lace segment 24. The overlapped portions joined to one another by any suitable fastening arrangement, such as stitching 28.

Figure 5:
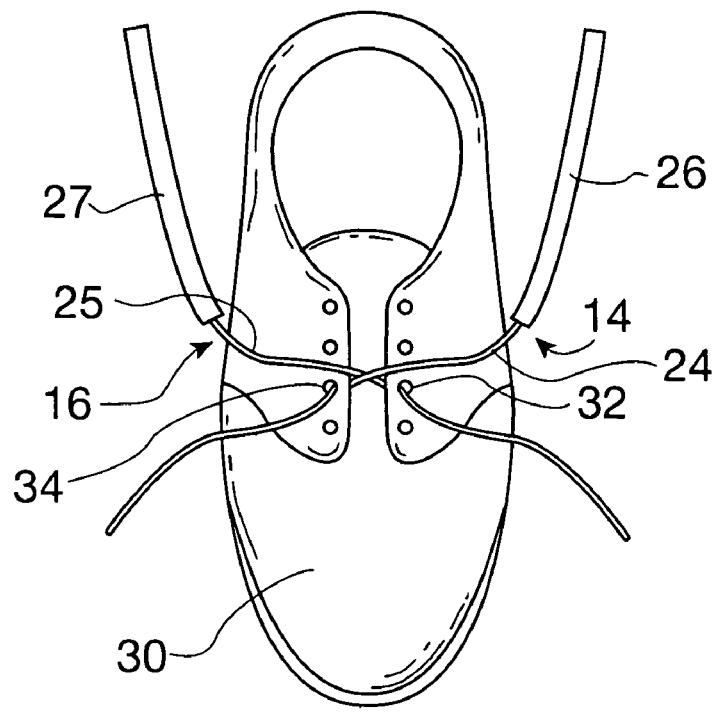
FIG. 5 is a reduced scale dorsal view of a shoe, illustrating the manner in which the laces are about to be secured at lower shoelace eyelets.

The free end of the lace segment 24 of the medial support strap 14 is secured to a medial aspect of the vamp of a shoe 30 by being threaded through a lower medial shoe eyelet 34, as illustrated in FIG. 5. It should be appreciated that the shoe 30, illustrated in FIGS. 1, 5, 6, 7 and 9 comprises a left shoe, although the shoe style may differ slightly in appearance in the various views.

Similarly, the lateral support strap 16 includes a lace segment 25 and a hook fastener strip 27. The free end of the lace segment 25 is secured to the lateral aspect of the vamp of the shoe 30 by being threaded through a lower shoelace eyelet 32.

For the purpose of simplification, conventional shoelaces 36 are depicted only in FIG. 1. It is intended, however, for the shoe 30 be conventionally laced with shoelaces extending through some or all of the remaining shoelace eyelets.

After the free ends of the lace segments 24, 25 have been threaded through the lower shoelace eyelets 32, 34, the lace segments are tied together with a bow or knot 35. The support straps 14, 16 are then secured to the cuff 12 after adjusting the effective lengths of the support straps for proper orientation of the foot.

Figure 6:
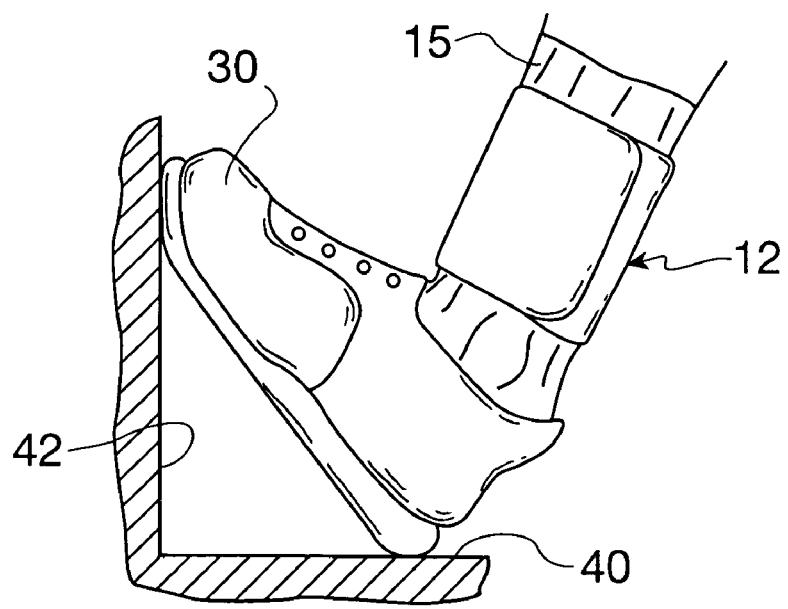
FIG. 6 is a side elevational view of a foot and ankle, with the cuff being wrapped about the ankle and the foot being positioned at an orientation for securement of support straps about the cuff, with the support straps being omitted for clarity.
Figure 7:
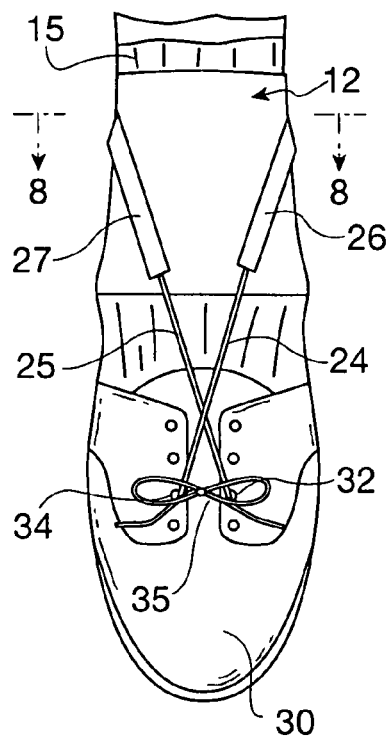
FIG. 7 is a dorsal view of a shoe, foot, ankle and cuff, with the ankle foot orthosis being fitted and with the conventional shoelace omitted for clarity.
Figure 8:
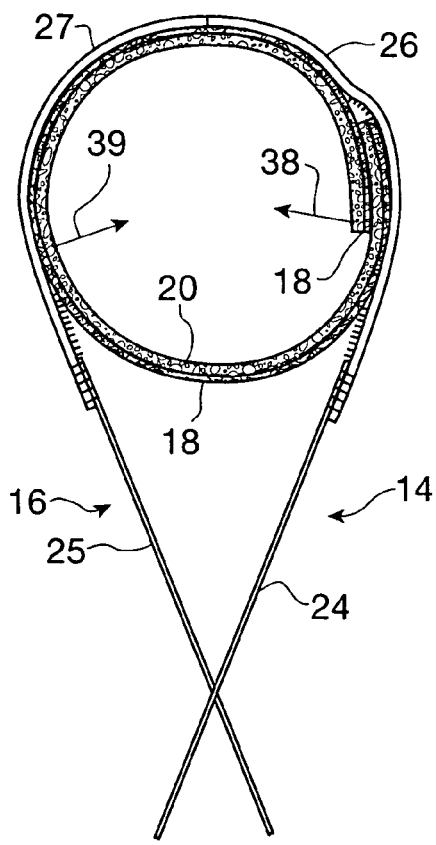
FIG. 8 is an enlarge scale sectional view through the ankle foot orthosis, the same being taken substantially along the line 8-8 of FIG. 7 and showing the cuff wrapped about the ankle and the support strap fastener strips wrapped about the cuff.

With attention now directed to FIG. 6, wherein a typical technique for assuring proper foot/ankle orientation for securement of the fastening straps is illustrated, one places the heel of one's shoe on a floor support surface 40, close to a vertical upright wall 42, with the shoe toe resting against the wall 42 and may assume an acute angle, e.g. 85° between the sole of the foot and the tibia axis. Alternatively, the toe portion of one's shoe is raised by resting on a block or other support.

Thereafter, the medial support strap 14 is drawn taut and the hooks of the hook fastener strip 26 are engaged in the exposed looped fibers of the cuff 12 at the lateral side of the ankle. The remaining length of the hook fastener strip is wrapped about the rear of the cuff 12. Similarly, the lateral support strap 16 is held taut and the hook portion of the fastener strip 27 engages the cuff 12 about the medial side of the ankle and is wrapped rearwardly. Because of the employment of hook and loop type fasteners, with virtually infinitely variable fastening points, the effective lengths of the support straps are precisely fixed for user's anatomy.

When the foot is thereafter raised, the support straps tension and their lengths adjust to maintain the foot at the proper orientation, i.e. with the sole of the foot substantially perpendicular to the tibia axis. If the foot is not properly oriented, the support straps are removed and reapplied with the foot positioned at a different angular orientation.

The cuff 12 thus creates an anchoring locus for the support straps 26, 27. The tensile force necessary to support the foot in an orientation substantially perpendicular to the axis of the tibia and transmitted through each of the crossed support straps includes radial vector components 38, 39. The entire tensile load is diffused through the compressible foam substrate 20 and distributed around the ankle, including at the lateral and medical sides, so as to reduce strain at the rear of the ankle and the Achilles tendon.

Figure 9:
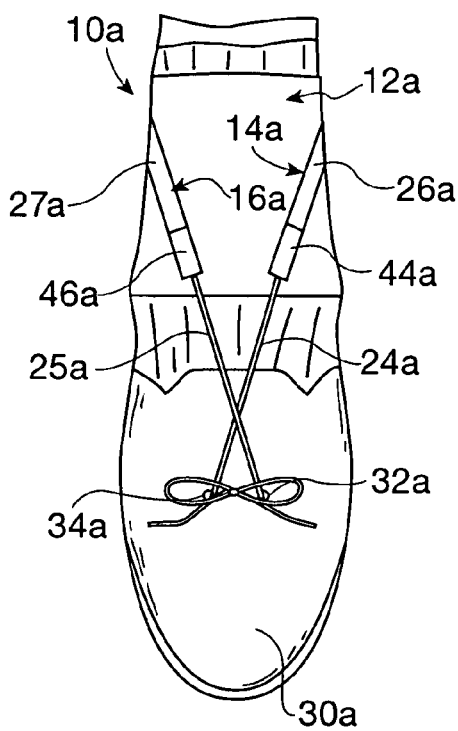
FIG. 9 is a dorsal view of an alternate embodiment of a fitted ankle foot orthosis, similar to FIG. 7, however with modified support straps having an elastic segment between each lace and each fastener strip and also showing a laceless shoe which has been adapted to accommodate the support straps.

In FIG. 9 there is illustrated an alternate embodiment of the invention wherein like numerals have been employed to denote like components of the previous embodiment, however, bearing the suffix "a".

The alternate embodiment of an ankle foot orthosis 10a includes a cuff 12a, substantially identical to the cuff 12 previously described, as well as a pair of dorsiflexion support straps, 14a, 16a. The dorsiflexion support straps 14a, 16a each include a lace segment 24a, 25a and a fastener strip 26a, 27a. The support strap 14a includes, however, a yieldable elastic segment 44a, interconnecting the lace segment 24a and the fastener strip 26a. Similarly, the support strap 16a includes an elastic segment 46a, interconnecting the lace segment 25a and the fastener strip 27a. The elastic segments 44a, 46a permit extension of the effective length of the respective support straps 14a, 16a so as to permit the toe portion of one's foot to move downward, as may be necessary when one steps down from a curb or other elevated surface.

The embodiment of FIG. 9 also illustrates a mode of employment of the ankle foot orthosis for use in conjunction with a shoe 30a, which does not have shoelace eyelets, such as a loafer or slipper. In such event, it is possible to punch, drill or cut suitable eyelets 32a, 34a through the shoe vamp.

Alternately, one may employ strip fastener segments at the vamp ends of the lace portions and affix mating loop fabric segments to the shoe vamp. A further vamp attachment variation is to have the entire length of the support straps comprised of a hook fastener strip. The lace portions of the straps may also be fastened to a shoe vamp by stitching, adhesive, snaps, buckles and the like.

Thus is will be seen that there is provided an ankle foot orthosis which achieves the various aspects, features and considerations of the present invention and which is well suited to meet the conditions of practical usage.

Since various possible embodiments might be made of the present invention and since various changes might be made in the exemplary embodiments set forth herein without departing from the spirit of the invention, it is to be understood that all matter herein described or shown in the accompanying drawings is deemed to be interpreted as illustrative and not in a limiting sense.

The invention claimed is:

1. An ankle foot orthosis for remediation of foot drop symptoms of an afflicted foot, the orthosis comprising a cuff configured for securement about and anatomically conforming to the shape of the ankle of the afflicted foot and a conventional shoe worn over the afflicted foot, the cuff comprising a flexible laminated panel having an outer layer and a compressible foam substrate, the outer layer including a surface configured for hook and loop type fastener securement, a pair of dorsiflexion support straps, each strap including a lace portion threaded through a shoelace eyelet for securement to the vamp portion of the conventional shoe and a fastener strip portion, the lace portion of each strap being narrower than the fastener strip portion, the fastener strip portion being compatible with the outer layer surface, the fastener strip portion of one strap engaging the surface at a medial side of the ankle and being wrapped rearwardly about the surface and secured thereto by hook and loop type fastener engagement, the fastener strip portion of the other strap engaging the surface at a lateral side of the ankle and being wrapped rearwardly about the surface and secured thereto by hook and loop type fastener engagement, the lace portion of the one strap being threaded through a shoelace eyelet at a lateral aspect of the shoe vamp and the lace portion of the other strap being threaded through a shoelace eyelet at a medial aspect of the shoe vamp, tensile force for remediation of foot drop symptoms being transmitted from the vamp to the cuff through the support straps.

2. An ankle foot orthosis for remediation of foot drop symptoms as constructed in accordance with claim 1 wherein the surface includes loop fibers and the fastener strip portions comprise hook elements.

3. An ankle foot orthosis for remediation of foot drop symptoms as constructed in accordance with claim 1 wherein the cuff is positioned over a sock.

4. An ankle foot orthosis for remediation of foot drop symptoms as constructed in accordance with claim 1 wherein the foam substrate comprises an open cell foam.

5. An ankle foot orthosis for remediation of foot drop symptoms as constructed in accordance with claim 1 wherein the foam substrate comprises a closed cell foam.

6. An ankle foot orthosis for remediation of foot drop symptoms as constructed in accordance with claim 1 wherein the lace portions of both straps are tied together.

7. An ankle foot orthosis for remediation of foot drop symptoms as constructed in accordance with claim 1 wherein each support strap includes an elastic portion intermediate the lace portion and the fastener strip portion.

8. An ankle foot orthosis for remediation of foot drop symptoms as constructed in accordance with claim 1 wherein the cuff comprises a stretchable panel which is wrapped about the ankle.

9. A method of providing dorsiflexion support to a foot afflicted with foot drop, the foot being covered with a shoe, the method comprising the steps of:

a) providing a stretchable panel having first hook and loop fastener elements and a pair of straps, each strap having a lace portion comprising a single lace and a fastener strip portion comprising second hook and loop fastener elements, b) wrapping the panel about the ankle of the afflicted foot to form a cuff, c) threading one end of the lace portion of a first strap through a shoelace eyelet in a vamp portion of the shoe, d) threading one end of the lace portion of a second strap through a shoelace eyelet in a vamp portion of the shoe, the vamp portions being laterally spaced from one another, e) tying the threaded ends of the lace portions together in a bow or knot, and f) attaching the fastener strip portions of the support straps to opposite sides of the cuff by engaging the first and second hook and loop fastener elements, g) distributing the tensile force necessary to remediate foot drop through the lace portion and the fastener strip portion of each support strap.

10. A method of providing dorsiflexion support to a foot afflicted with foot drop in accordance with claim 9 wherein the first hook and loop fastener elements comprise a fabric layer having a looped fiber outer surface, the second hook and loop fastener elements include hook elements and step (e) is performed by pressing hook elements of each support strap against the looped fiber outer surface.

11. A method of providing dorsiflexion support to a foot afflicted with foot drop in accordance with claim 9 wherein the foot is appended from a leg having a tibia axis, the method further including the step of orienting the afflicted foot at an acute angle relative to the tibia axis prior to performing step (e).

12. An orthotic appliance for supporting a foot afflicted with foot drop systems, the afflicted foot wearing a conventional shoe, the appliance including a stretchable cuff wrapped about the ankle of the afflicted foot and a pair of dorsiflexor support straps, each strap having a lace portion threaded through an eyelet extending through the vamp of the shoe, each strap having a fastener strip portion, the lace portion being narrower than the fastener strip portion, the fastener strip portion having a transverse dimension greater than the diameter of the eyelet, the cuff including an inner compressible foam substrate and an outer layer, the lace portion of one strap being threaded through an eyelet on the medial aspect of the vamp of the shoe, the lace portion of the other strap being threaded through an eyelet on the lateral aspect of the vamp, the lace portions being tied together, the straps crossing each other above the vamp, the fastener strip portion of the one strap being secured to the outer layer of the cuff on the lateral side of the ankle, the fastener strip portion of the other strap being secured to the outer layer of the cuff on the medial side of the ankle, the force necessary for supporting the afflicted foot being transmitted from the vamp to the ankle through the support straps and the cuff.

13. An orthotic appliance as constructed in accordance with claim 12 wherein the lace portion and the fastener strip portion of each strap are joined together by stitching.

14. An orthotic appliance as constructed in accordance with claim 12 further including an elastic segment intermediate the lace portion and the fastener strip portion of each strap.

15. An orthotic appliance as constructed in accordance with claim 12 wherein the cuff comprises a laminated panel which is secured in wrapped position by a hook and loop fastener.

16. An orthotic appliance as constructed in accordance with claim 12 wherein the lace portions are tied together in a bow or knot.

\* \* \* \* \*